US008658831B2

(12) United States Patent
Heinrich et al.

(10) Patent No.: US 8,658,831 B2
(45) Date of Patent: Feb. 25, 2014

(54) METHOD FOR SEPARATING N,N-DIALKYLBISAMINOALKYLETHER FROM MIXTURES COMPRISING N,N-DIALKYLBISAMINOALKYLBISAMINOALKYLETHER AND AT LEAST ONE OF N,N,N'-TRIALKYLBISAMINOALKYLETHER AND N,N,N',N'-TETRAALKYLBISAMINOALKYLETHER

(75) Inventors: Humbert Heiko Heinrich, Hamburg (DE); Gaspar Zsolt, Petfurdo (HU); Felber Gabor, Veszprem (HU); Gaspar Attila, Petfurdo (HU); Grigsby Robert Alison, Jr., East Legends Trail Spring, TX (US); Kordas Imre, Veszpreme (HU); Vanderstraeten Petra Emma, Leuven (BE)

(73) Assignees: Huntsman International LLC, The Woodlands, TX (US); Huntsman Corporation Hungary ZRT, Petfurdo (HU)

( * ) Notice: Subject to any disclaimer, the term of this patent is extended or adjusted under 35 U.S.C. 154(b) by 108 days.

(21) Appl. No.: 13/375,494

(22) PCT Filed: May 6, 2010

(86) PCT No.: PCT/EP2010/056143
§ 371 (c)(1),
(2), (4) Date: Feb. 14, 2012

(87) PCT Pub. No.: WO2010/139520
PCT Pub. Date: Dec. 9, 2010

(65) Prior Publication Data
US 2012/0130132 A1 May 24, 2012

Related U.S. Application Data

(60) Provisional application No. 61/183,165, filed on Jun. 2, 2009.

(30) Foreign Application Priority Data

Jun. 29, 2009 (EP) .................................... 09462006

(51) Int. Cl.
*C07C 209/86* (2006.01)

(52) U.S. Cl.
USPC .......................................................... 564/499

(58) Field of Classification Search
USPC .......................................................... 564/499
See application file for complete search history.

(56) References Cited

U.S. PATENT DOCUMENTS

| 1,898,461 | A | * | 2/1933 | Nicodemus et al. | 564/499 |
| 2,657,237 | A | * | 10/1953 | Isham | 564/499 |
| 4,174,351 | A | * | 11/1979 | Shoffner | 564/425 |
| 5,189,221 | A | * | 2/1993 | Duranleau et al. | 564/499 |
| 5,292,958 | A | * | 3/1994 | Claud et al. | 564/499 |
| 6,011,156 | A | * | 1/2000 | Matson | 546/184 |
| 6,353,138 | B1 | * | 3/2002 | Rooney | 564/497 |

FOREIGN PATENT DOCUMENTS

| EP | 1849789 | 10/2007 |
| EP | 0322982 | 7/2009 |
| WO | 01/58848 | 8/2001 |
| WO | 2008/140957 | 11/2008 |

OTHER PUBLICATIONS

International Search Report and Written Opinion regarding corresponding application No. PCT/EP2010/056143, dated Jul. 5, 2010.

* cited by examiner

*Primary Examiner* — Brian J Davis
(74) *Attorney, Agent, or Firm* — Monique M. Raub

(57) ABSTRACT

According to the present invention, a method for separating a primary amine being an N,N-dialkylbisaminoalkylether, from mixtures comprising said primary amine and at least one of a secondary amine being an N,N,N'-trialkylbisaminoalkylether and a tertiary amine being an N,N,N',N'-tetraalkylbisaminoalkylether, comprising the steps:

(α) joining said mixture and at least one of a ketone and an aldehyde for reacting said primary amine with said at least one of a ketone and an aldehyde, thereby providing a primary amine based imine by a Schiff base reaction;

(β) separating the primary amine based imine from said at least one of the secondary or tertiary amine; and (γ) recovering the primary amine from its primary amine based imine by hydrolysis of the primary amine based imine.

15 Claims, 1 Drawing Sheet

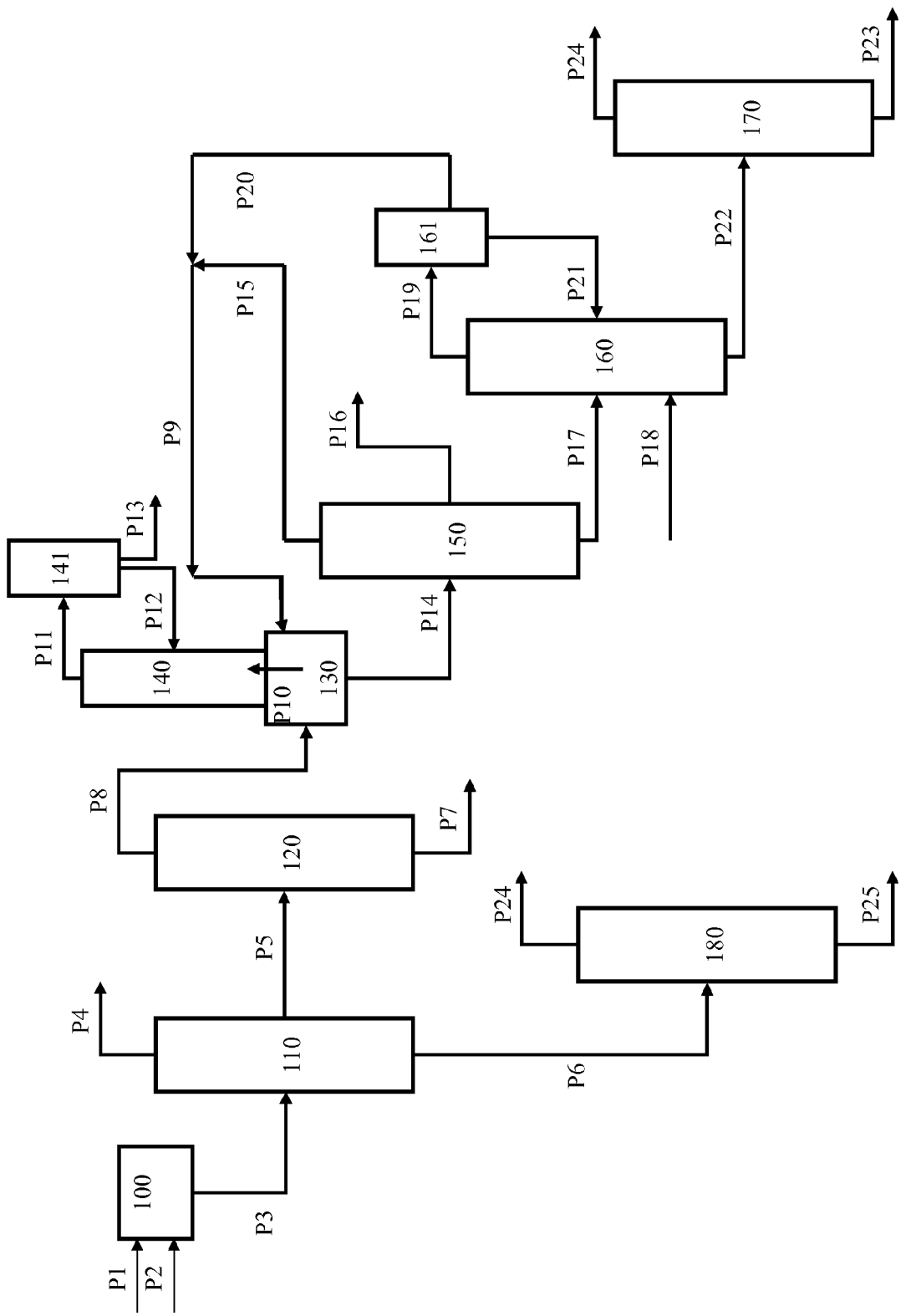

METHOD FOR SEPARATING N,N-DIALKYLBISAMINOALKYLETHER FROM MIXTURES COMPRISING N,N-DIALKYLBISAMINOALKYLBISAMINOALKYLETHER AND AT LEAST ONE OF N,N,N'-TRIALKYLBISAMINOALKYLETHER AND N,N,N',N'-TETRAALKYLBISAMINOALKYLETHER

CROSS-REFERENCE TO RELATED APPLICATION

This application is the National Phase of International Application PCT/EP2010/056143 filed May 6, 2010 which designated the U.S. and which claims priority to Foreign Application No. 09462006.9 filed Jun. 29, 2009 and U.S. Provisional Application No. 61/183,165 filed Jun. 2, 2009. The noted applications are incorporated herein by reference.

The present invention relates to separation or recovering N,N-2-dialkylbisaminoalkylethers from a mixture further comprising at least one of a secondary amine or a tertiary amine, such as at least one of N,N,N'-trialkylbisaminoalkylether and N,N,N',N'-tetraalkylbisaminoalkylether or a mixture of one or more such N,N,N'-trialkylbisaminoalkylethers and N,N,N',N'-tetraalkylbisaminoalkylethers.

In particular, the invention relates to methods for separating or recovering primary amines, with formula $R^{11}R^{12}NR^{13}NH_2$, from mixtures comprising the primary amine or amines and at least one of a secondary amine, with formula $R^{21}R^{22}NR^{23}NHR^{24}$, and a tertiary amine, with formula $R^{31}R^{32}NR^{33}NR^{34}R^{35}$ or a mixture of one or more such secondary amines and one or more of such tertiary amines, for which, as the case may be,

- each of $R^{11}$, $R^{21}$ and/or $R^{31}$, each of the $R^{12}$, $R^{22}$ and/or $R^{32}$ being alkyl groups chosen from the group consisting of a methyl group, an ethyl group, an iso-propyl group or an n-propyl group;
- each of $R^{24}$ and/or $R^{34}$ and $R^{35}$ being alkyl groups chosen from the group consisting of a methyl group, an ethyl group, an iso-propyl group and an n-propyl group;
- each of $R^{13}$, $R^{23}$ and/or $R^{33}$ being an alkoxyalkyl group chosen from the group consisting of ethoxyethyl, ethoxy-n-propyl and n-propoxy-n-propyl.

An example of such mixture is a mixture of N,N-dimethylbisaminoethylether (T2MBAEE), N,N,N'-trimethylbisaminoethylether (T3MBAEE) and/or N,N,N',N'-tetramethylbisaminoethylether (T4MBAEE), from which N,N-dimethylbisaminoethylether can be separated or recovered according to the present invention.

Various N,N-2-dialkylbisaminoalkylethers, N,N,N'-trialkylbisaminoalkylethers and N,N,N',N'-tetraalkylbisaminoalkylethers are known as chemical compounds.

In particular, at least some primary amines, with formula $R^{11}R^{12}NR^{13}NH_2$, secondary amines with formula $R^{21}R^{22}NR^{23}NHR^{24}$, and tertiary amines with formula $R^{31}R^{32}NR^{33}NR^{34}R^{35}$ for which

- each of $R^{11}$, $R^{21}$, $R^{31}$, $R^{12}$, $R^{22}$ and $R^{32}$ being alkyl groups chosen from the group consisting of a methyl group, an ethyl group, an iso-propyl group or an n-propyl group;
- each of $R^{24}$, $R^{34}$ and $R^{35}$ being alkyl groups chosen from the group consisting of a methyl group, an ethyl group, an iso-propyl group and an n-propyl group;
- each of $R^{13}$, $R^{23}$ and $R^{33}$ being an alkoxyalkyl group chosen from the group consisting of ethoxyethyl, ethoxy-n-propyl and n-propoxy-n-propyl are known chemical compounds, often being present in a mixture.

Typically, $R^{11}$, $R^{21}$ and $R^{31}$ are identical as well as $R^{12}$, $R^{22}$ and $R^{32}$ being identical and $R^{13}$, $R^{23}$ and $R^{33}$ being identical, and $R^{24}$ and $R^{34}$ being identical.

Some of the above amines are known and used as polyurethane catalysts or as precursors for the provision of polyurethane catalysts.

In general, very often blends or mixtures of such primary, secondary and tertiary amines are obtained in industrial processes for providing the primary, secondary or tertiary amine.

In particular, mixtures of a primary amine being an N,N-dialkylbisaminoalkylether, e.g. N,N-dimethylbisaminoethylether (T2MBAEE), a secondary amine being an N,N,N'-trialkylbisaminoalkylether, e.g. N,N,N'-trimethylbisaminoethylether (T3MBAEE), and/or a tertiary amine being an N,N,N',N'-tetraalkylbisaminoalkylether, e.g. N,N,N',N'-tetramethylbisaminoethylether (T4MBAEE), may be obtained.

For instance, N,N,N'-trimethylbisaminoethylether (T3MBAEE) is an important chemical compound and can be used as a precursor for the manufacturing of catalysts.

N,N,N',N'-tetramethylbisaminoethylether (T4MBAEE) on its turn is a known polyurethane catalyst, sold by Huntsman International LLC under the trade name JEFFCAT® ZF20. N,N,N'-trimethylbisaminoethylether (T3MBAEE) and N,N,N',N'-tetramethylbisaminoethylether (T4MBAEE) are typically obtained simultaneously in the same process, their ratio depending on a.o. process settings and products used. N,N,N'-trimethylbisaminoethylether (T3MBAEE) and N,N,N',N'-tetramethylbisaminoethylether (T4MBAEE) have fairly close boiling points and cannot be separated by distillation.

Typically, N,N-dimethylbisaminoethylether (T2MBAEE) is also present in the blend of N,N,N',N'-tetramethylbisaminoethylether and N,N,N'-trimethylbisaminoethylether as an impurity, and also has a boiling point fairly close to the boiling points of N,N,N',N'-tetramethylbisaminoethylether and N,N,N'-trimethylbisaminoethylether. T2MBAEE cannot be distillated from this blend neither.

However, for quality reasons it is important to provide customers with highly purified N,N,N',N'-tetramethylbisaminoethylether and likewise there is a high economic interest to recover the T2MBAEE and T3MBAEE, because they might be used as a starting material for other high valuable chemical components.

Further, there is, at present, no economically acceptable production process for providing T2MBAEE, nor is there a process which enables to economically separate T2MBAEE from mixtures of T2MBAEE, T3MBAEE and T4MBAEE for providing high purity compounds. More in general, at present there is a need for a process for separating primary amine such as N,N-dialkylbisaminoalkylether from mixtures of this primary amine, a secondary amine such as N,N,N'-trialkylbisaminoalkylether and/or a tertiary amine such as N,N,N',N'-tetraalkylbisaminoalkylether.

Further, as at present T2MBAEE is only present as an impurity in the mixtures of T2MBAEE, T3MBAEE and T4MBAEE, there is a need for a production process to provide T2MBAEE, in which N,N-dialkylbisaminoalkylether is provided in substantive quantities as final product.

It is an object of the present invention to provide a method for separating or recovering N,N-2-dialkylbisaminoalkylethers from a mixture further comprising at least one of a secondary amine or a tertiary amine, such as at least one of N,N,N'-trialkylbisaminoalkylether and N,N,N',N'-tetraalkylbisaminoalkylether or a mixture of one or more such N,N,N'-trialkylbisaminoalkylethers and N,N,N',N'-tetraalkylbisaminoalkylethers, which method provides the primary amine in substantially pure form and on industrially acceptable yield.

The above objective is accomplished by a method according to the present invention.

According to a first aspect of the present invention, a method for separating a primary amine being an N,N-dialkylbisaminoalkylether, from mixtures comprising said primary amine and at least one of a secondary amine being an N,N,N'-trialkylbisaminoalkylether and a tertiary amine being an N,N,N',N'-tetraalkylbisaminoalkylether is provided. The method comprises the steps:

(α) joining said mixture and at least one of a ketone and an aldehyde for reacting said primary amine with said at least one of a ketone and an aldehyde, thereby providing a primary amine based imine by a Schiff base reaction;

(β) separating the primary amine based imine from said at least one of the secondary or tertiary amine by distillation; and (γ) recovering the primary amine from its primary amine based imine by hydrolysis of the primary amine based imine.

Preferably, the N,N-dialkylbisaminoalkylether is N,N-dimethylbisaminoethylether, also referred to as T2MBAEE, and said mixture further comprises at least one of the secondary amine N,N,N'-trimethylbisaminoethylether, also referred to as T3MBAEE and the tertiary amine N,N,N',N'-tetramethylbisaminoethylether, also referred to as T4MBAEE.

The primary amine being an N,N-dialkylbisaminoalkylether, and at least one of a secondary amine being an N,N,N'-trialkylbisaminoalkylether and a tertiary amine being an N,N,N',N'-tetraalkylbisaminoalkylether are typically well soluable in water and in organic media. When imines are formed using ketones or aldehydes, preferably aliphatic ketones or aliphatic aldehydes, these imines are typically also well soluable in water and organic media.

However, it was found that the obtained imines can be separated from said at least one of the secondary or tertiary amine by distillation said at least one of the secondary or tertiary amine from the mixture of the primary amine based imine and said at least one of the secondary or tertiary amine. This again in particular in case aliphatic ketones and/or aliphatic aldehydes are used in the Schiff base reaction forming the imine based upon the primary amine.

According to some embodiments of the present invention, the largest difference between the boiling points of the primary amine and the at least one of a secondary amine and a tertiary amine may be less than 10° C.

According to some embodiments of the present invention, the smallest difference between the boiling point of the primary amine based imine and the boiling points of the primary amine, the at least one of a secondary amine and a tertiary amine may be more than 10° C.

According to some embodiments of the present invention, the primary amine may have a formula $R^{11}R^{12}NR^{13}NH_2$, the secondary amine having formula $R^{21}R^{22}NR^{23}NHR^{24}$ and/or said tertiary amine having formula $R^{31}R^{32}NR^{33}NR^{34}R^{35}$, for which each of $R^{11}$, $R^{21}$ and/or $R^{31}$, $R^{12}$, $R^{22}$ and/or $R^{32}$ being alkyl groups chosen from the group consisting of a methyl group, an ethyl group, an iso-propyl group or an n-propyl group;

each of $R^{24}$ and/or $R^{34}$ and $R^{35}$ being alkyl groups chosen from the group consisting of a methyl group, an ethyl group, an iso-propyl group and an n-propyl group;

each of $R^{13}$, $R^{23}$ and/or $R^{33}$ being an alkoxyalkyl group chosen from the group consisting of $-CH_2CH_2OCH_2CH_2-$, (also referred to as ethoxy-ethyl), $-CH_2CH_2OCH_2CH_2CH_2-$ (also referred to as ethoxy-n-propyl) and $-CH_2CH_2CH_2OCH_2CH_2CH_2-$ (also referred to as n-propoxy-n-propyl).

It was found that by providing a primary amine based imine from the primary amine, the physical properties can be changed to such an extent that separation becomes more easy to perform. As an example, typically the boiling point of the primary amine based imine is higher than the one of the primary amine itself. By increasing the boiling point, the boiling points of the primary amine based imine and the secondary and/or tertiary amine may become sufficiently remote to allow distillation of the secondary an/or tertiary amine from the primary amine based imine. By simply hydrolyzing the primary amine based imine, the primary amine can be obtained.

It is understood that it is the invention is in particularly useful to separate a primary amine with formula $R^{11}R^{12}NR^{13}NH_2$ from a secondary amine with formula $R^{21}R^{22}NR^{23}NHR^{24}$ and/or a tertiary amine with formula $R^{31}R^{32}NR^{33}NR^{34}R^{35}$. Optionally, and even preferably, the groups $R^{11}$, $R^{12}$ and $R^{13}$ of the primary amine are identical to the corresponding groups of the secondary and/or tertiary amine, i.e. $R^{21}$, $R^{22}$ and $R^{23}$ respectively $R^{31}$, $R^{32}$ and $R^{33}$. In case the mixture comprises both secondary and tertiary amines, the group $R^{24}$ of the secondary amine is identical to the corresponding group $R^{34}$ of the tertiary amine.

According to some embodiments of the present invention, each of $R^{11}$ may be identical to $R^{21}$ and/or $R^{31}$, $R^{12}$ being identical to $R^{22}$ and/or $R^{32}$ and $R^{13}$ being identical to $R^{23}$ and/or $R^{33}$.

According to some embodiments of the present invention, the mixture may comprise the primary amine, a secondary amine with formula $R^{21}R^{22}NR^{23}NHR^{24}$ and a tertiary amine with formula $R^{31}R^{32}NR^{33}NR^{34}R^{35}$, $R^{24}$ being identical to $R^{34}$.

Optionally, $R^{11}$ may be identical to $R^{21}$ and $R^{31}$, $R^{12}$ may be identical to $R^{22}$ and $R^{32}$ and $R^{13}$ may be identical to $R^{23}$ and $R^{33}$.

According to some embodiments of the present invention, the mixture may comprise a secondary amine and a tertiary amine.

According to some embodiments of the present invention, the method further may comprise separating the N,N,N'-trialkylbisaminoalkylether from the N,N,N',N'-tetraalkylbisaminoalkylether by a) amidation of N,N,N'-trialkylbisaminoalkylether to obtain an N,N,N'-trialkylbisaminoalkylether-based amide;

b) separating N,N,N',N'-tetraalkylbisaminoalkylether from the N,N,N'-trialkylbisaminoalkylether-based amide;

c) transamidation of the N,N,N'-trialkylbisaminoalkylether-based amide with a transamidation agent selected form the group consisting of ammonia, primary and/or secondary amines with the proviso that the transamidation agent is not N,N,N'-trialkylbisaminoalkylether;

d) separation of N,N,N'-trialkylbisaminoalkylether from the reaction mixture obtained by said transamidation, optionally by fractionated azeotropic and/or fractionated non-azeotropic distillation.

According to some embodiments of the present invention, the mixture may comprise at least one of N,N,N'-trimethylbisaminoethylether and N,N,N',N'-tetramethylbisaminoethylether.

According to some embodiments of the present invention, the N,N-dialkylbisaminoalkylether may be N,N-dimethylbisaminoethylether.

According to some embodiments of the present invention, the mixture may comprise N,N,N'-trimethylbisaminoethylether, N,N,N',N'-tetramethylbisaminoethylether or both N,N,N'-trimethylbisaminoethylether and N,N,N',N'-tetramethylbisaminoethylether.

Separating of an N,N,N'-trialkylbisaminoalkylether from an N,N,N',N'-tetraalkylbisaminoalkylether in general can be obtained by
a) amidation of N,N,N'-trialkylbisaminoalkylether to obtain an N,N,N'-trialkylbisaminoalkylether-based amide;
b) separating N,N,N',N'-tetraalkylbisaminoalkylether from the N,N,N'-trialkylbisaminoalkylether-based amide;
c) transamidation of the N,N,N'-trialkylbisaminoalkylether-based amide with a transamidation agent selected form the group consisting of ammonia, primary and/or secondary amines with the proviso that the transamidation agent is not N,N,N'-trialkylbisaminoalkylether;
d) separation of N,N,N'-trialkylbisaminoalkylether from the reaction mixture obtained by said transamidation, optionally by fractionated azeotropic and/or fractionated non-azeotropic distillation.

This process is hereafter explained for separation of N,N,N',N'-tetramethylbisaminoethylether from blends of N,N,N',N'-tetramethylbisaminoethylether and N,N,N'-trimethylbisaminoethylether, though the skilled man understands that the principle applies for blends of N,N,N'-trialkylbisaminoalkylether and N,N,N',N'-tetraalkylbisaminoalkylether.

In general N,N,N'-trimethylbisaminoethylether is present as a side product in the manufacturing process for N,N,N',N'-tetramethylbisaminoethylether which is a catalyst used in the production of polyurethane foam. Blends of N,N,N',N'-tetramethylbisaminoethylether and N,N,N'-trimethylbisaminoethylether are formed when methylamines comprising a mixture of monomethylamine, dimethylamine and trimethylamine are reacted with diethylene glycole over a copper chromite catalyst. The ratio of these materials may vary by a wide range depending on the composition of methylamines (ratio of dimethylamine versus monomethylamine). Due to the fact, that N,N,N',N'-tetramethylbisaminoethylether and N,N,N'-trimethylbisaminoethylether have boiling points which differ from each other only slightly any distillative purification is extremely difficult.

Derivatisation of T3MBAEE is technically difficult and/or uneconomic because no pure T3MBAEE is available for synthetic purposes. The prior art only provides blends which cause technical problems if recycling of N,N,N'-trimethylbisaminoethylether is required. This is because the separation by distillation will yield a blend of the same materials, however, having a different composition.

A method to separate N,N,N',N'-tetramethylbisaminoethylether from N,N,N'-trimethylbisaminoethylether is provided in the co-pending patent application WO2008140957 from Huntsman International LLC, hereby incorporated by reference in its entirety.

The first step in the method for separating these secondary amines from the tertiary amines, such as N,N,N'-trimethylbisaminoethylether from mixtures comprising at least one tertiary amine or tertiary aminoalkylether, is the amidation of N,N,N'-trimethylbisaminoethylether to obtain an N,N,N'-trimethylbisaminoethylether-based amide.

A representative example of a tertiary aminoalkylether is N,N,N',N'-tetramethylbisaminoethylether (or bis-(2-dimethylaminoethyl)ether). In principle the amidation of N,N,N'-trimethylbisaminoethylether (IUPAC-name: N,N-dimethyl-2-[2'-(methylamine)ethoxy]ethanamine), can be carried out by any technique known to the person skilled in the art. Preferably, amidation of N,N,N'-trimethylbisaminoethylether is carried out with a carboxylic acid and/or carboxylic acid derivative selected from the group consisting of acylhalide, anhydride, carboxylic esters and carboxylic amides. Examples of suitable carboxylic acid derivatives are acetylhalides such as acetylchloride and acetylbromide, acetic acid anhydride, formic acid ester, acetic acid esters, formamide and acetamide. Preferably the amidation step is carried out with a low molecular weight carboxylic acid, preferably a $C_{1-6}$-carboxylic acid, more preferably acetic acid or formic acid. Particularly, the formation of the corresponding formamide of N,N,N'-trimethylbisaminoethylether is preferred.

After the amidation of N,N,N'-trimethylbisaminoethylether has been performed the tertiary amines or tertiary aminoalkylethers which have not been amidated can be separated from the amide obtained in amidation step. Separation of amide from the mixture comprising at least one tertiary amine and/or tertiary aminoalkylether can in principle be carried out by any known separation technique. Preferably this separation step is carried out by distillation, preferably at a temperature from 50 to 250° C. at 1 mbar to 1 bar, preferably at 5 mbar to 1 bar.

The formamide of T3MBAEE which can be obtained by amidation of T3MBAEE with formic acid can preferably be separated from N,N,N',N'-tetramethylbisaminoethylether by distillation of N,N,N',N'-tetramethylbisaminoethylether wherein—due to the higher boiling point—the formamide remains in the distillation residue. Subsequently, the remaining formamide can also be distilled in order to obtain the pure T3MBAEE formamide.

Further, recovering N,N,N'-trimethylbisaminoethylether from its amide may be obtained by the following steps:
(a) Transamidation of the amide with a transamidation agent selected form the group consisting of ammonia, primary and/or secondary amines with the proviso that the transamidation agent is not N,N,N'-trimethylbisaminoethylether;
(b) Separation of N,N,N'-trimethylbisaminoethylether from the reaction mixture obtained in step by fractionated azeotropic and/or fractionated non-azeotropic distillation.

The transamidation agent may be selected from the group consisting of ammonia, primary and/or secondary amines.

Preferred transamidation agents are presented by formula (I):

$$R^3\underset{k}{\left(\underset{n}{\left(\underset{H_2}{C}\right)}\right)}\underset{R^4}{\overset{R^4}{\underset{|}{C}}}-X_a\underset{m}{\left(\underset{H_2}{\left(\underset{H_2}{C}\right)}\overset{R^4}{\underset{|}{CH}}\right)}-Y_b\underset{o}{\left(\underset{H_2}{C}\right)}-R^5 \quad \text{wherein}$$

$R^3 =$ —H, —CH$_3$, —N(CH$_3$)$_2$, cyclohexyl, piperidinyl, pyrrolidinyl (N), morpholinyl, piperazinyl, cyclopentyl, pyrrolidinyl, phenyl $R^4 =$ —H, —CH$_3$, ethyl, propyl, iso-propyl, linear or branched $C_{4-12}$-alkyl;

$R^5=R^3$, —OH, —$NH_2$, —$OCH_3$, —$N(CH_3)_2$
X=Y=O—, —NH—, —$N(CH_3)$—
k=integer from 0 to 35, preferably 1 to 20, more preferably 2 to 10
l=integer from 0 to 5
m=0 or 1
n=integer from 0 to 30, preferably 1 to 24, more preferably 10 to 18
o=0 or 1
a=0 or 1
b=0 or 1
with the proviso that the transamidation agent comprises at least one nitrogen-hydrogen bond (N—H) and with the proviso that the transamidation agent is not N,N,N'-trimethylbisaminoethylether.

Transamidation agents according to formula (I) are preferred with k=1 and n=an integer from 10 to 30. In case n=0 or 1, k in formula (I) is preferably an integer from 1 to 35, more preferably k is an integer from 2 to 20.

Particularly, preferred transamidation agents are polyalkoxyleneamines or fatty amines.

Preferred transamidation agents are primary or secondary alkanolamines. Primary alkanolamines are preferably selected from the group consisting of monoethanolamine, 1,3-propanolamine, isopropanolamine as well as $C_{4-8}$-alkanolamines. Secondary alkanolamines are preferably selected from the group consisting of diethanolamine, N-methylethanolamine, N-ethylethanolamine, N-propylethanolamine, N-isopropylethanolamine, N-methylisopropanolamine, N-ethylisopropanolamine, N-isopropylisopropanolamine, N-$C_1$-$C_6$-alkyl-N-$C_2$-$C_6$-alkanolamine, N,N-di-$C_2$-$C_1$-$C_6$-alkanolamine.

Particularly, preferred are alkanolamines selected from the group consisting of monoethanolamine, 2(2-aminoethoxy)-ethanol, N-methylethanolamine, monoisopropanolamine, aminopropane-3-ol, N-ethylethanolamine, N-propylethanolamine, aminobutane-4-ol, N-2-hydroxyethylaniline, N-hydroxyethylpiperazine.

In a further preferred embodiment of the present invention the transamidation agent is selected from the group consisting of substituted and unsubstituted primary and/or secondary alkylamines or arylamines.

The primary alkylamines are preferably selected from the group consisting of methylamine, ethylamine, propylamine, isopropylamine, cyclohexylamine, cyclopentylamine, $C_4$-$C_{18}$ alkylamine, $C_4$-$C_6$ cycloalkylamine The secondary alkylamines are preferably selected from the group consisting of dimethylamine, diethylamine, methylethylamine, $C_1$-$C_6$-alkyl-$C_1$-$C_6$-alkylamine, cycloaliphatic compounds comprising at least one nitrogen atom in the cycle such as pyrrolidone, piperazine, imidazoline and morpholine.

Particularly, preferred are transamidation agents selected from the group consisting of monomethylamine, isopropylamine, aminobutane, aminooctane, aminododecane, aminooctadecane, cyclohexylamine, N-methylcyclohexylamine, N-ethylcyclohexylamine, N,N-dicyclohexylamine, cyclopentylamine, N-methylcyclopentylamine, ethylcyclopentylamine, piperidine, pyrrolidine, aniline, 1,2-diaminoethane, diethylenetriamine, triethylenetetramine, bis-[3-(dimethylamino-propyl]-amine, N-aminoethylpiperazine, 1,3-dimethylaminopropaneamine, 1-methoxypropane-3-amine, butoxypropane-3-amine, (2-dimethylaminoethoxy)-3-propanamine, morpholine, N-aminopropylmorpholine and aminoethoxyethylmorpholine.

Further, ammonia, preferably aqueous ammonia is a suitable transamidation agent.

A method according to this first aspect of the present invention has the advantage that N,N-dialkylbisaminoalkylether, such as N,N-dimethylbisaminoethylether, may be obtained with a purity of more than 95 w %, even more then 97.5 w %, such as more than 99 w %. These purities can be obtained when providing N,N-dialkylbisaminoalkylether, such as N,N-dimethylbisaminoethylether, at economically acceptable conditions, when run on industrial scale.

According to some embodiments of the present invention, the Schiff base reaction step (α) of the method according to the first aspect of the present invention, may be carried out with a ketone, preferably MIBK.

The Schiff base reaction can be carried out with various ketones and/or aldehydes, but aliphatic ketones or aliphatic aldehydes, most preferably methylisobutylketone (also known as 4-methyl-2-pentanone and MIBK), are preferred.

Aliphatic ketones or aliphatic aldehydes such as e.g. cyclohexanone, valeraldehyde, 2-methylcyclopentanone, cyclopentanone, 3-methyl-2-butanone, 2-methylcyclohexanone, 4-methylcyclohexanone, isovaleraldehyde, 3-methylcyclohexanone, trimethylacetaldehyde, 3,3 dimethylbutan-2one, isobutyraldehyde, 2-butanone (known as MEK), 2-methylbutyraldehyde, 4-methyl-2-pentanone, diethylketone, methylbutylketone and methylisopropylketone may be used.

Alternatively, though less preferred, furfurylaldehyde and benzaldehyde might be used. These aromatic aldehydes are more difficult to separate from the primary amine after hydrolysation of the primary amine based imine.

Preferably the used ketones and/or aldehydes, preferably aliphatic ketones or aldehydes, provide an azeotrope with water. This allows the removal of the ketones and/or aldehydes from the primary amine after hydrolysation of the primary amine based imine by adding water to the primary amine based imine, preferably an excess of water. A mixture of water, the primary amine and the ketones and/or aldehydes is obtained. After removal of the ketones and/or aldehydes by azeotrope distillation, a mixture of the primary amine and water is obtained.

According to some embodiments of the present invention, the resulting primary amine based imine may be separated from the at least one of a secondary amine or a tertiary amine by distillation.

According to some embodiments of the present invention, recovering the primary amine from its primary amine based imine may comprise adding an excess of water to the primary amine based imine.

According to some embodiments of the present invention, recovering the primary amine from its primary amine based imine may comprise adding an excess of water to the primary amine based imine, thereby providing the primary amine, water and the at least one of a ketone and an aldehyde. Optionally, e.g. as is the case using the ketone MIBK, an azeotrope of water and the at least one of a ketone and an aldehyde may be provided. Optionally, an additional solvent may be added to remove the water.

The ketone, such as MIBK, and water may be separated from the primary amine, such as N,N-dimethylbisaminoethylether, by distillation, thereby providing a stream of water and the at least one of a ketone and an aldehyde, optionally a water/ketone azeotrope such as water/MIBK azeotrope. Hence the distillation is then an azeotrope distillation. The latter applies in particular in case of use of MIBK. The MIBK may be recycled and reused in the Schiff base reaction. Also the water may be recycled and reused for recovering the primary amine, such as N,N-dimethylbisaminoethylether from the formed the primary amine based imine.

The obtained primary amine, such as N,N-dimethylbisaminoethylether may further be refined by distillation, which at the end may provide a primary amine, such as N,N-dimethylbisaminoethylether with a purity of even more than 99 w %.

According to a second aspect of the present invention, an N,N-dialkylbisaminoalkylether, such as N,N-dimethylbisaminoethylether is provided. The N,N-dialkylbisaminoalkylether, such as N,N-dimethylbisaminoethylether, may comprise traces of entraining solvent, optionally being MIBK, or traces of N,N,N'-trimethylbisaminoethylether, N,N,N',N'-tetramethylbisaminoethylether or N,N-2-dimethylaminoethoxyethanol.

An N,N-dialkylbisaminoalkylether, obtainable according to the first aspect of the present invention is provided.

According to a third aspect of the present invention N,N-dialkylbisaminoalkylether, obtained according to the first aspect of the present invention may be used as catalyst in the production of polyurethane.

The method for separating primary amines according to the present invention has the advantage that a primary amine with formula $R^{11}R^{12}NR^{13}NH_2$ such as N,N-dialkylbisaminoalkylether, e.g. N,N-dimethylbisaminoethylether, can be provided with a high degree of purity, and this in an economically acceptable manner.

According to a fourth aspect of the present invention, a method for producing a primary amine being an N,N-dialkylbisaminoalkylether, from mixtures comprising said primary amine and at least one of a secondary amine being an N,N,N'-trialkylbisaminoalkylether and a tertiary amine being an N,N,N',N'-tetraalkylbisaminoalkylether is provided. The method comprises the steps:

(α) Providing a mixture comprising N,N-dialkylbisaminoalkylether, and at least one of a secondary amine being an N,N,N'-trialkylbisaminoalkylether and a tertiary amine being an N,N,N',N'-tetraalkylbisaminoalkylether;

Separating said primary amine from said mixture by a method according to the first aspect of the present invention.

According to some embodiments of the present invention, the primary amine may have formula $R^{11}R^{12}NR^{13}NH_2$, the secondary amine having formula $R^{21}R^{22}NR^{23}NHR^{24}$ and/or the tertiary amine having formula $R^{31}R^{32}NR^{33}NR^{34}R^{35}$, for which each of $R^{11}$, $R^{21}$ and/or $R^{31}$, $R^{12}$, $R^{22}$ and/or $R^{32}$ being alkyl groups chosen from the group consisting of a methyl group, an ethyl group, an iso-propyl group or an n-propyl group;

each of $R^{24}$ and/or $R^{34}$ and $R^{35}$ being alkyl groups chosen from the group consisting of a methyl group, an ethyl group, an iso-propyl group and an n-propyl group;

each of $R^{13}$, $R^{23}$ and/or $R^{33}$ being an alkoxyalkyl group chosen from the group consisting of —CH$_2$CH$_2$OCH$_2$CH$_2$—, —CH$_2$CH$_2$OCH$_2$CH$_2$CH$_2$— and —CH$_2$CH$_2$CH$_2$OCH$_2$CH$_2$CH$_2$—

According to some embodiments of the present invention, the mixture may be provided by reacting dialkylaminoalkoxyalkanol with ammonia.

According to some embodiments of the present invention, reacting dialkylaminoalkoxyalkanol with ammonia may be done in presence of a catalyst According to some embodiments of the present invention, the mixture may be provided by reacting dialkyleneglycol with at least one selected from the group consisting of ammonia, monoalkylamine and dialkylamine.

According to some embodiments of the present invention, bis-(N,N-dialkylaminoalkoxyalkyl)amine may be separated from the mixture, optionally before separating the primary amine from the mixture.

This separation of the dimer can be done by distillation of the mixture prior to adding the ketone or aldehyde to the mixture to obtain the Schiff base reaction of this ketone or aldehyde with the N,N-dialkylbisaminoalkylether.

A significant stream of bis-(N,N-dialkylaminoalkoxyalkyl)amine is obtained in case the mixture, comprising bis-(N,N-dialkylaminoalkoxyalkyl)amine, is provided by reacting ammonia with dialkylaminoalkoxyalkanol.

The independent and dependent claims set out particular and preferred features of the invention. Features from the dependent claims may be combined with features of the independent or other dependent claims as appropriate.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

FIG. 1 shows schematically a reaction scheme of a method according to the invention for separating a primary amine with formula $R^{11}R^{12}NR^{13}NH_2$ from a mixture of said primary amine and at least a secondary and/or tertiary amine, and a method for producing said primary amine.

The present invention will be described with respect to particular embodiments.

It is to be noticed that the term "comprising", used in the claims, should not be interpreted as being restricted to the means listed thereafter; it does not exclude other elements or steps. It is thus to be interpreted as specifying the presence of the stated features, steps or components as referred to, but does not preclude the presence or addition of one or more other features, steps or components, or groups thereof. Thus, the scope of the expression "a device comprising means A and B" should not be limited to devices consisting only of components A and B. It means that with respect to the present invention, the only relevant components of the device are A and B.

Throughout this specification, reference to "one embodiment" or "an embodiment" are made. Such references indicate that a particular feature, described in relation to the embodiment is included in at least one embodiment of the present invention. Thus, appearances of the phrases "in one embodiment" or "in an embodiment" in various places throughout this specification are not necessarily all referring to the same embodiment, though they could. Furthermore, the particular features or characteristics may be combined in any suitable manner in one or more embodiments, as would be apparent to one of ordinary skill in the art from this disclosure.

The following terms are provided solely to aid in the understanding of the invention.

The term "alkylether" is to be understood as a linear or branched aliphatic group comprising carbon and at least one, but optionally more than one ether-bond. Alkylethers with only one ether-bond are preferred.

When reference is made to boiling points or boiling temperature, unless otherwise indicated, the boiling point or boiling temperature indicates the boiling point or boiling temperature under atmospheric pressure.

Unless otherwise indicated, any percentage of a component refers to weight percentages over the total weight of the substance in which the individual component is present.

The various aspects of the present invention will further be described in detail by means of one or more examples relating to the separation of T2MBAEE from mixtures of T2MBAEE, T3MBAEE and T4MBAEE. The skilled person however understands that the same principle applies for separation of primary amines with formula $R^{11}R^{12}NR^{13}NH_2$, from secondary amines with formula $R^{21}R^{22}NR^{23}NHR^{24}$ and tertiary amines with formula $R^{31}R^{32}NR^{33}NR^{34}R^{35}$, for which

- each of $R^{11}$, $R^{21}$ and/or $R^{31}$, $R^{12}$, $R^{22}$ and/or $R^{32}$ being alkyl groups chosen from the group consisting of a methyl group, an ethyl group, an iso-propyl group or an n-propyl group;
- each of $R^{24}$ and/or $R^{34}$ and $R^{35}$ being alkyl groups chosen from the group consisting of a methyl group, an ethyl group, an iso-propyl group and an n-propyl group;
- each of $R^{13}$, $R^{23}$ and/or $R^{33}$ being an alkoxyalkyl group chosen from the group consisting of ethoxyethyl, ethoxy-n-propyl and n-propoxy-n-propyl.

Even more in general, the skilled person understands this example can be applied to separation or recovering N,N-2-dialkylbisaminoalkylethers from a mixture further comprising at least one of a secondary amine or a tertiary amine, such as at least one of N,N,N'-trialkylbisaminoalkylether and N,N,N',N'-tetraalkylbisaminoalkylether or a mixture of one or more such N,N,N'-trialkylbisaminoalkylethers and N,N,N',N'-tetraalkylbisaminoalkylethers In particular, the processes according to the present invention are useful for primary, secondary and/or tertiary amine mixtures wherein $R^{11}$, $R^{21}$ and $R^{31}$ are identical, $R^{12}$, $R^{22}$ and $R^{32}$ are identical, $R^{13}$, $R^{23}$ and $R^{33}$ are identical, and $R^{24}$ and $R^{34}$ are identical.

According to an aspect of the present invention, N,N-2-dimethylaminoethoxyethylamine, (also referred to as N,N-dimethylaminoethoxyethylamine, T2 or T2MBAEE), was synthesized by reacting N,N-2-dimethyl-aminoethoxyethanol with ammonia over a copper-chromite catalyst. The reaction scheme looks like:

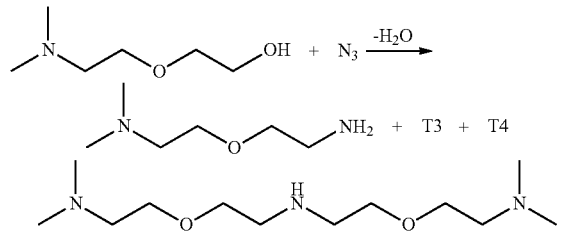

wherein T3 refers to N,N,N'-trimethylbisaminoethylether (or T3MBAEE) and wherein T4 refers to N,N,N',N'-tetramethylbisaminoethylether (also known as T4MBAEE or JEFFCAT® ZF-20). N,N-2-dimethyl-aminoethoxyethanol is also known as JEFFCAT® ZR-70.

In the reactor effluent the following materials were identified:

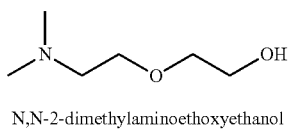

N,N-2-dimethylaminoethoxyethanol

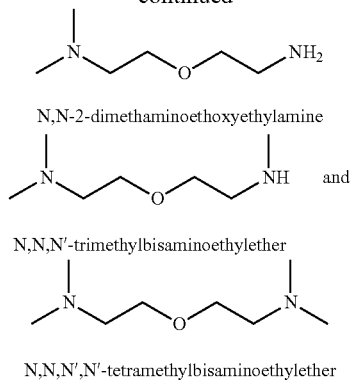

N,N-2-dimethaminoethoxyethylamine

N,N,N'-trimethylbisaminoethylether

N,N,N',N'-tetramethylbisaminoethylether

Also, a dimerized form of T2 was detected in the reactor effluent as a main component, which is:

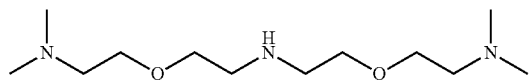

being bis-(N,N-2-dimethylaminoethoxyethyl)amine (hereinafter also referred to as "T22" or "T2-dimer"). T22 has a molar weight MW of 247. T22 may be understood to be a tetramethylated derivative of N,N-bis(2-aminoethoxyethyl-)amine.

Further other components were identified as various compounds structurally similar to bis-(N,N-2-dimethylamino-ethoxy-ethyl)-amine, e.g. the methylated derivative of N,N-bis(2-aminoethoxyethyl-)amine, having the structure:

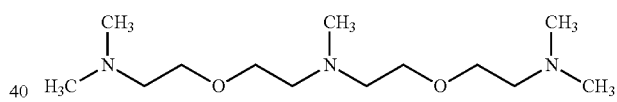

i.e. bis-(N,N-2-dimethylaminoethoxyethyl-1)methylamine (also referred to as "TM22") or by UPAC nomenclature: 2,8,14-triaza-5,11-dioxa-2,8,14-trimethyl-pentadecane), MW 261.

Further components having a similar structure as T22 are

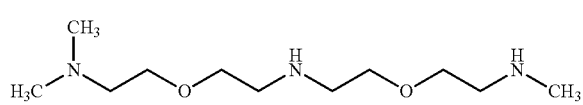

[2-(2-Dimethylamino-ethoxy)-ethyl]-[2-(2-methylamino-ethoxy)-ethyl]-amine or by UPAC nomenclature: 2,8,14-triaza-5,11-dioxa-2-methyl-pentadecane, MW 233, and

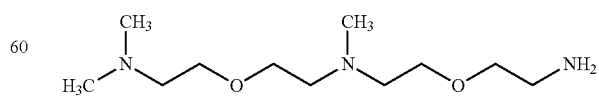

[2-(2-Amino-ethoxy)-ethyl]-[2-(2-dimethylamino-ethoxy)-ethyl]-methyl-amine or by UPAC nomenclature: 2,8,14-triaza-5,11-dioxa-2,8-dimethyl-tetradecane; MW 233, and some minor amount of

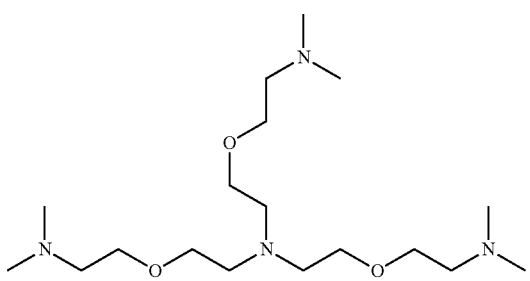

[2-(2-{Bis-[2-(2-dimethylamino-ethoxy)-ethyl]-amino}-ethoxy)-ethyl]-dimethyl-amine; MW 362.

The reactor effluent was split by distillation into three fractions:

- a light fraction, consisting of water and morpholines.
- a middle fraction containing mainly a blend of N,N-2-dimethylaminoethoxyethylamine, N,N,N'-trimethylbisaminoethylether, N,N,N',N'-tetramethylbisaminoethylether and N,N-2-dimethylaminoethoxyethanol; and
- a heavy fraction consisting mainly of bis-(N,N-2-dimethylaminoethoxyethyl)amine and some other by-products, such as the various compounds structurally similar to bis-(N,N-2-dimethylamino-ethoxy-ethyl)-amine mentioned above.

In the middle fraction the products T2, T3 and T4 were found, whereas in the heavy fraction bis-(N,N-2-dimethylaminoethoxyethyl)amine is contained by ca. 85 wt.-% (w % over total weight of heavy fraction). Two other by-products (in total ca. 15 wt.-%) were found in that material. According to GC/MS analysis these materials are having very similar structures as T22.

Depending on the reaction conditions of the amination of N,N-2-dimethylaminoethoxyethanol with ammonia, a wide range of ratios of T2/T3/T4 may be obtained in the middle fraction. In all experiments done, T2, T3 and T4 were present. As an example the ratio T2/T3/T4 can be 3.6/1/1.3.

An attempt to split the product mix of N,N-2-dimethylaminoethoxyethylamine, N,N,N'-trimethylbis-aminoethylether and N,N,N',N'-tetramethylbisaminoethylether by distillation was conducted but found to be inappropriate to separate the three compounds. Distillation feed and distillate showed within the analytically error practically identical compositions. Seen the substantially identical boiling points of the components, distillation cannot be done on industrial scale. The boiling point of T2 is about 191° C., the boiling point of T3 is about 190° C. and the boiling point of T4 is about 189° C.

The content of N,N-2-dimethylaminoethoxyethylamine in the mixture is significant. Combining the method according to the present invention to separate a primary amine from secondary and tertiary amines with the method to product T2 by reacting N,N-dimethyl-aminoethoxyethanol with ammonia over a catalyst, e.g. a copper-chromite catalyst, gives an economically acceptable method to produce T2.

Alternative methods to provide mixtures comprising T2, T3 and T4 are methods based upon reacting diethyleneglycol or with a starting amine, as set out in the table 1 under.

TABLE 1

| Group | diethyleneglycol and starting amine | ratios of T4/T3/T2 by weight | | |
|---|---|---|---|---|
| | | T4 | T3 | T2 |
| 1 | dimethylamine | 27.5 | 1 | ≤0.03 |
| 2 | monomethylamine | 7.4 | 24 | 1 |
| 3 | ammonia | 1.7 | 1 | 10 |

It is clear that the ratio T2:T3:T4 may vary significantly, depending on the starting amine with whom the diethyleneglycol is reacted. It is clear that the starting amine may be selected in function of the product to be synthesized.

The groups as shown in table 1 contain always the same components, but in different concentrations.

Group 1

In the case of synthesis of N,N,N',N'-tetramethylbisaminoethylether, the content of N,N-2-dimethylaminoethoxyethylamine is low (usually <0.1% w). Though technically possible, no particular separation effort is needed to eliminate N,N-2-dimethylaminoethoxyethylamine from the mixture. The only need exists to reduce the N,N,N'-trimethylbisaminoethylether content, which may be done by the method as was set out above, by means of amidation and transamidation.

Group 2

In the case of synthesis of N,N,N'-trimethylbisaminoethylether, N,N,N',N'-tetramethyl-bisaminoethylether is obtained in substantial quantity as by-product. When using amidation and transamidation as set out above to separate N,N,N'-trimethylbisaminoethylether from N,N,N',N'-tetramethylbisaminoethylether, substantially pure N,N,N',N'-tetramethylbisaminoethylether is obtained.

Obviously N,N,N'-trimethylbisaminoethylether and N,N-2-dimethylaminoethoxyethylamine are transferred in to the corresponding formamides. In the subsequent transamidation reaction, like N,N,N'-trimethylbisaminoethylether, N,N-2-dimethylaminoethoxyethylamine is able to form an azeotrope with monoethanolamine, too. The recovered N,N,N'-trimethylbisaminoethylether may contain up to 5% N,N-2-dimethylaminoethoxyethylamine. Thus the amidation and transamidation steps are not satisfying for separation and recovery of both materials individually. The N,N-2-dimethylaminoethoxyethylamine present in N,N,N'-trimethylbisaminoethylether is highly undesired, because it could cause various complications in the further utilization of N,N,N'-trimethylbisaminoethylether.

Group 3

In the case of the synthesis of N,N-2-dimethylaminoethoxyethylamine, both N,N,N'-trimethylbisaminoethylether and N,N,N',N'-tetramethylbisaminoethylether show up as byproducts. For the further utilization of N,N-2-dimethylaminoethoxyethylamine, a strong need exists to isolate and purify the N,N-2-dimethylaminoethoxyethylamine.

Separating N,N-2-dimethylaminoethoxyethylamine from the mixture of N,N-2-dimethylaminoethoxyethylamine, N,N,N'-trimethylbisaminoethylether and/or N,N,N',N'-tetramethylbisaminoethylether blends, independent of its origin, and isolate the components contained as substantially pure products, may be done according to the present invention by capping N,N-2-dimethylaminoethoxyethylamine by suitable carbonyl compounds to form a Schiff base. After removal of the uncapped N,N,N'-trimethylbisaminoethylether and/or N,N,N',N'-tetramethylbisaminoethylether by distillation, both the carbonyl compound and N,N-2-dimethylaminoethoxyethylamine are recovered as substantially pure materials by hydrolysis.

Further separating N,N,N'-trimethylbisaminoethylether and N,N,N',N'-tetramethylbisaminoethylether may be done by amidation and trandamidation of the N,N,N'-trimethylbisaminoethylether and N,N,N',N'-tetramethylbisaminoethylether blend, thereby providing N,N,N'-trimethylbisaminoethylether and N,N,N',N'-tetramethylbisaminoethylether.

In case of N,N-2-dimethylaminoethoxyethylamine, essentially all N,N-2-dimethylaminoethoxyethylamine contained in the reactor effluent was recovered. The separation of the product mixture was in particular obtained by using MIBK via a Schiff base formation by following reaction scheme.

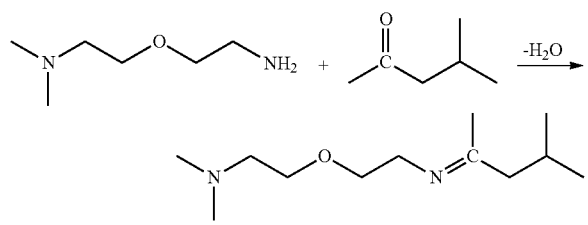

MIBK-Schiff base of T2, being {2-[2-(1,3-Dimethyl-butylideneamino)-ethoxy]-ethyl}-dimethyl-amine.

This T2-based imine has a boiling point estimated above 300° C. A boiling point of 160 to 161° C. was measured at 1 mbar vacuum.

This way, after the Schiff base is formed by dewatering, a mixture of N,N,N'-trimethylbisaminoethylether and N,N,N',N'-tetramethylbisaminoethylether is removed by vacuum distillation from the high boiling Schiff base. Thereafter, the remaining Schiff base is hydrolyzed back by a large excess of water and simultaneously removal of the formed MIBK by an azeotropic distillation. Substantially pure N,N-2-dimethylaminoethoxyethylamine is remaining in the distillation flask and optionally a subsequent fine fractionation delivers purified N,N-2-dimethylbisaminoethylether.

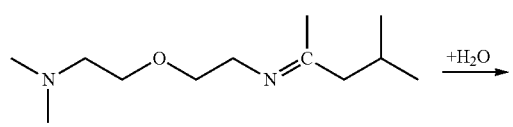

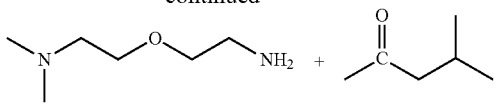

The recovered N,N-2-dimethylaminoethoxyethylamine shows after distillation a purity of 99+ wt.-%, whereas the N,N,N'-trimethylbisaminoethylether/N,N,N',N'-tetramethylbisaminoethylether mixture was substantially free of N,N-2-dimethylaminoethoxyethylamine.

For Schiff base reaction, MIBK (methylisobutylketone) can be replaced by various other carbonyl compounds. Other carbonyl compounds are e.g. cyclohexanone, isovaleraldehyde and alike. In case of MIBK, no azeotropic entraining agent is necessary, because MIBK acts as both as reagent for the Schiff base formation and as entraining agent as well. If other carbonyl compounds are chosen usually suitable entraining solvents are needed, preferably being hydrocarbons, such as methylcyclohexane, toluene or xylene or a xylene isomer blend.

The production and separation of N,N-2-dimethylaminoethoxyethylamine, N,N,N'-trimethylbisaminoethylether, N,N,N',N'-tetramethylbisaminoethylether and bis-(N,N-2-dimethylaminoethoxyethyl)amine is hereafter further explained by means of examples 1 to 4.

EXAMPLE 1

Provision of T2/T3/T4 Mixture by Reacting dimethylaminoethoxyethanol with Ammonia A 1000 ml stainless steel reactor was charged with 2000 g commercial 2CuOxCr$_2$O$_3$ catalyst (CAS#99328-50-4, from Aldrich). The head of the continuous reactor system was connected with separate inlet lines and feed pumps for liquid ammonia and dimethylaminoethoxyethanol.

Ammonia and N,N-2-dimethylaminoethoxyethanol were charged to the reactor at different reaction conditions, as shown in Table 2. The reactor effluents were taken off at the bottom of the reactor, depressurized, degassed and collected for analysis and further use. All running conditions and compositions of the reactor effluents are shown in Table 2.

TABLE 2

| Running conditions and product composition | | | | | | | |
|---|---|---|---|---|---|---|---|
| | unit | Run 1 | Run 2 | Run 3 | Run 4 | Run 5 |
| Reaction conditions | | | | | | | |
| Reactor temperature | ° C. | 170 | 180 | 190 | 200 | 170 |
| Reactor pressure | bar | 70 | 70 | 70 | 70 | 70 |
| Catalyst load | | | | | | | |
| ammonia | ltr/h | 0.1 | 0.1 | 0.1 | 0.1 | 0.1 |
| N,N-2-dimethylaminoethoxyethanol | ltr/h | 0.5 | 0.5 | 0.5 | 0.5 | 0.13 |
| Mol ratio ammonia versus N,N-2-dimethylaminoethoxyethanol | | 1.6:1 | 1.6:1 | 1.6:1 | 1.6:1 | 6:1 |
| Product composition [wt.-%] | | | | | | | |
| Compound | | | | | | | |
| morpholine | [wt.-%] | 0.18 | 0.53 | 0.79 | 1.12 | 0.37 |
| N-methylmorpholine | [wt.-%] | 0.26 | 0.70 | 1.16 | 1.89 | 0.30 |
| N,N-2-dimethylaminoethoxyethylamine | [wt.-%] | 6.63 | 6.61 | 8.60 | 7.96 | 13.88 |
| N,N,N'-trimethylbisaminoethylether | [wt.-%] | 0.38 | 0.95 | 1.69 | 2.31 | 0.08 |
| N,N,N',N'-tetramethylbisaminoethylether | [wt.-%] | 0.52 | 1.71 | 1.80 | 2.71 | 0.40 |

TABLE 2-continued

| Running conditions and product composition | | | | | | |
|---|---|---|---|---|---|---|
| | unit | Run 1 | Run 2 | Run 3 | Run 4 | Run 5 |
| N,N-2-dimethylaminoethoxyethanol | [wt.-%] | 79.32 | 67.34 | 52.92 | 47.23 | 51.48 |
| bis-(N,N-2-dimethylaminoethoxyethyl)amine | [wt.-%] | 9.25 | 13.18 | 20.82 | 21.14 | 25.60 |
| compounds structurally similar to bis-(N,N-2-dimethylamino-ethoxy-ethyl)-amine | [wt.-%] | 3.64 | 8.98 | 12.22 | 15.64 | 7.12 |

All reactor effluents were combined (resulting in 8500 g crude material) and fractioned on a batch-type distillation tower, containing structured packings, having a total packing length of 100 cm. A main split was carried out to divide the combined reactor effluents in to three fractions. Fraction#1 and fraction#2 were collected as overhead products, whereas fraction#3 was taken as the residue stream.

Fraction#1 was containing all reaction water and various light boiling components like morpholine, N-methylmorpholine and others. Fraction#2 contained mainly N,N-2-dimethylaminoethoxyethylamine, N,N,N'-trimethylbisaminoethylether, N,N,N',N'-tetramethylbisaminoethylether, and N,N-2-dimethyl-aminoethoxyethanol. Working conditions and results of the main split distillation are shown in Table 3.

TABLE 3

| Conditions and results of main splitting distillation forming fractions #1 and fraction #2 | | | |
|---|---|---|---|
| | unit | fraction #1, Example 1 | fraction #2, Example 1 |
| Boiling range, head temperature | ° C. | 48-98 | 98-133 |
| Boiling range, pot temperature | ° C. | 92-143 | 143-145 |
| Pressure | mbar | 100 | 100 |
| Reflux:take off ratio (vapour divider) | | 05:01 | 15:01 |
| product composition [wt.-%] *) | | | |
| morpholine | [wt.-%] | nd | 0.43 |
| N-methylmorpholine | [wt.-%] | nd | 0.22 |
| N,N-2-dimethylaminoethoxyethylamine (=A) | [wt.-%] | nd | 40.07 |
| N,N,N'-trimethylbis-aminoethylether (=B) | [wt.-%] | nd | 11.01 |
| N,N,N',N'-tetramethylbisaminoethylether (=C) | [wt.-%] | nd | 14.70 |
| N,N-2-dimethylaminoethoxyethanol | [wt.-%] | nd | 29.51 |
| bis-(N,N-2-dimethylaminoethoxyethyl)amine | [wt.-%] | nd | 0.01 |
| compounds structurally similar to bis-(N,N-2-dimethylamino-ethoxy-ethyl)-amine | [wt.-%] | nd | 4.05 |
| Ratio A:B:C | | nd | 40:11:15 |

*) = based on water free material
nd = not determined

The bottom fraction was retained as residue fraction#3. GC-analysis of this residue-fraction#3, showed that it consists mainly of bis-(N,N-2-dimethylaminoethoxyethyl) amine and some other components. Further examination and analysis showed that these other components are structurally similar to bis-(N,N-2-dimethylaminoethoxyethyl)amine, some being identified as

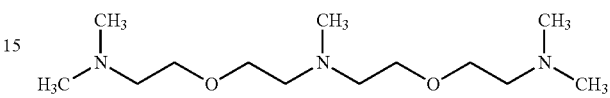

bis-(N,N-2-dimethylaminoethoxyethyl-1)methylamine (also referred to as "TM22") or by UPAC nomenclature: 2,8,14-triaza-5,11-dioxa-2,8,14-trimethyl-pentadecane), MW 261, and

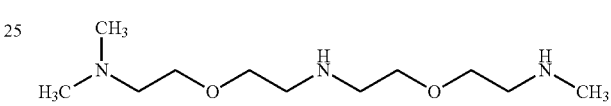

[2-(2-Dimethylamino-ethoxy)-ethyl]-[2-(2-methylamino-ethoxy)-ethyl]-amine or by UPAC nomenclature: 2,8,14-triaza-5,11-dioxa-2-methyl-pentadecane.

There are indications that another trace-impurity in T22 is

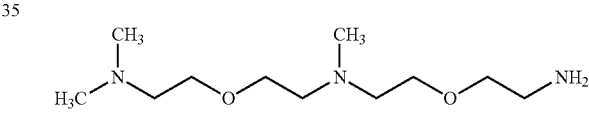

[2-(2-Amino-ethoxy)-ethyl]-[2-(2-dimethylamino-ethoxy)-ethyl]-methyl-amine or by UPAC nomenclature: 2,8,14-triaza-5,11-dioxa-2,8-dimethyl-tetradecane; MW 233

EXAMPLE 2

Isolation and Purification of N,N-2-dimethylaminoethoxyethylamine (T2MBAEE) Starting from Example 1/Fraction #2 by Fractionated Distillation A careful repeat of the distillation of fraction 2 of EXAMPLE 1 at 100 mbar and a reflux/take-off ratio of 20:1 was carried out. As result was obtained, that N,N-2-dimethylaminoethoxyethanol remained as bottom product whereas the aminoethers N,N-2-dimethylaminoethoxyethylamine (A), N,N,N'-trimethyl-bisaminoethylether (B) and N,N,N',N'-tetramethylbisaminoethylether (C) were collected in two fractions, namely fraction#1 of Example 2 and fraction#2 of Example 2.

The results, shown in Table 4, indicated that a fine fractionation by the conditions chosen, seems not to be sufficient to split the aminoethers N,N-2-dimethylaminoethoxyethylamine (A), N,N,N'-trimethyl-bisaminoethylether (B) and N,N,N',N'-tetramethylbisaminoethylether (C) in to pure single components.

TABLE 4

Conditions and results of fine fractionation of fraction #2/Example 1

|  | unit | Example 2, fraction #1 | Example 2, fraction #2 |
|---|---|---|---|
| Boiling range, head temperature | ° C. | 100-106 | 106 |
| Boiling range, pot temperature | ° C. | 121-124 | 124-130 |
| Pressure | mbar | 100 | 100 |
| Reflux:take off ratio (vapour divider) |  | 20:1 | 20:1 |
| product composition [wt.-%] *) | [wt.-%] |  |  |
| morpholine | [wt.-%] | 0.75 | 0.02 |
| N-methylmorpholine | [wt.-%] | 1.49 | 0.04 |
| N,N-2-dimethylaminoethoxyethylamine (=A) | [wt.-%] | 57.92 | 68.61 |
| N,N,N'-trimethylbis-aminoethylether (=B) | [wt.-%] | 6.17 | 10.5 |
| N,N,N',N'-tetramethylbisaminoethylether (=C) | [wt.-%] | 10.88 | 12.57 |
| N,N-2-dimethylaminoethoxyethanol | [wt.-%] | 0.01 | 0 |
| bis-(N,N-2-dimethylaminoethoxyethyl)amine | [wt.-%] | 0 | 0.01 |
| Other compounds | [wt.-%] | 22.78 | 8.26 |
| Ratio A:B:C |  | 9.4:1:1.8 | 6.5:1:0.8 |

*) = based on water free material
nd = not determined

EXAMPLE 3

Isolation and Purification of N,N-2-dimethylaminoethoxyethylamine (T2MBAEE) Starting from Fraction #2 of/Example 1 using methylisobutylketone A 2 liter reaction vessel was filled with 700 g fraction#2 of Example 1 (as produced by example 1) and 238.6 g methylisobutylketone. The reaction flask was connected to a packed distillation column, filled with structured packings (1 m packing length). The column head (vapour divider) was connected with a Dean-Starck trap, having an outlet for the water phase and a reflux line for the solvent.

The reaction mixture was heated to reflux and water formation started immediately. After the end of the water formation, totally 39.5 g of an aqueous phase were collected, having a water contend of 98.5 wt.-% water by KF titration.

The reaction mixture was cooled down and submitted to vacuum distillation. After complete removal of excess methylisobutylketone at a pressure of 100 mbar, all un-reacted N,N,N'-trimethylbisaminoethyl-ether (B) and N,N,N',N'-tetramethylbisaminoethyl-ether (C) were collected as a combined overhead product at 135° C./100 mbar until the head temperature started to rise significantly.

The distillate, containing all N,N,N'-trimethylbisaminoethylether (B) and N,N,N',N'-tetramethylbisamino-ethylether (C) was submitted to GC analysis and seen to be free of N,N-2-dimethylaminoethoxy-ethylamine. GC- and GC/MS-analysis showed that the bottom product was the substantially pure Schiff base and the JEFFCAT ZR 70, practically free from etheramines. Some traces of T4MBAEE, T3MBAEE and T2MBAEE are found, each being present in an amount less than <0.1 w %.

Thereafter, 1 l water was added to the reaction vessel and the Schiff base hydrolysed. Now, the water was recycled from the Dean-Stark trap, but the methylisobutylketone (MIBK) separated from the condensate. After the MIBK formation stopped, the reaction product was dewatered and further distilled in vacuum to distil the N,N-2-dimethylaminoethoxy-ethylamine from the other components in the mixture.

As such 102.8 g N,N-2-dimethylaminoethoxyethylamine having a purity of 99.6 wt.-% (by GC analysis) was collected. Other components are water, entraining solvent (MIBK), T3MBAEE and T4MBAEE. The structure of the product was verified by GC/MS. The estimated atmospheric boiling point is 190° C., the liquid density at 20° C. was determined as 0.86 g/ml.

EXAMPLE 4

Isolation and Purification of bis-(N,N-2-dimethylamino-ethoxyethyl)amine Starting from Example 1 Fraction #3

This residue fraction #3 of example 1 was distilled at different vacuum- and temperature conditions on a batch-type distillation tower, containing structured packings, having a total packing length of 100 cm. After a short transition fraction, fraction#4, two product fractions, fraction#5 and fraction#6 were taken.

Working conditions and results of distillation of residue-fraction#3 of example 1 are shown in Table 5.

TABLE 5 conditions and results of distillation of residue-fraction #3 of example 1

|  | unit | Example 1, fraction #4 | Example 1, fraction #5 | Example 1, fraction #6 |
|---|---|---|---|---|
| Boiling range, head temperature | ° C. | 20-20 | 120-125 | 125-128 |
| Boiling range, pot temperature | ° C. | 20-120 | 169-174 | 174-175 |
| Pressure | mbar | 7 | 7 | 7 |
| Reflux:take off ratio (vapour divider) |  | 2:1 | 2:1 | 2:1 |
| product composition [wt.-%] *) | [wt.-%] |  |  |  |
| morpholine | [wt.-%] | nd | 0 | 0 |
| N-methylmorpholine | [wt.-%] | nd | 0 | 0 |
| N,N-2-dimethylaminoethoxyethylamine (=A) | [wt.-%] | nd | 0 | 0 |
| N,N,N'-trimethylbis-aminoethylether (=B) | [wt.-%] | nd | 0 | 0 |
| N,N,N',N'-tetramethylbisaminoethylether (=C) | [wt.-%] | nd | 0 | 0 |

TABLE 5-continued conditions and results of distillation of residue-fraction #3 of example 1

|  | unit | Example 1, fraction #4 | Example 1, fraction #5 | Example 1, fraction #6 |
|---|---|---|---|---|
| N,N-2-dimethylaminoethoxyethanol | [wt.-%] | nd | 0.17 | 0.01 |
| bis-(N,N-2-dimethylaminoethoxyethyl)amine | [wt.-%] | nd | 83.83 | 81.02 |
| compounds structurally similar to bis-(N,N-2-dimethylamino-ethoxy-ethyl)-amine | [wt.-%] | nd | 16.0 | 18.97 |

*) = based on water free material
nd = not determined 868 g of fraction#5 of Example 1 were filled in to a 2 liter distillation flask of a batch type distillation tower containing structured packings (packing length=1 m).

A careful fractionation resulted 470.2 g of a product (table 6 fraction #2), containing 87.7 wt.-% bis-(N,N-2-dimethyl-aminoethoxyethyl)amine. Conditions and results are shown in Table 6.

TABLE 6

Conditions and results of fine fractionation of fraction #5/Example 1

|  | unit | fraction #1, | fraction #2, |
|---|---|---|---|
| Boiling range, head temperature | ° C. | 150-151 | 151-152 |
| Boiling range, pot temperature | ° C. | 173-174 | 174 |
| Pressure | mbar | 7 | 7 |
| Reflux:take off ratio (vapour divider) |  | 20:01 | 20:01 |
| product composition [wt.-%] *) | [wt.-%] |  |  |
| N,N-2-dimethylaminoethoxyethanol | [wt.-%] | nd | 0 |
| bis-(N,N-2-dimethylaminoethoxyethyl)amine | [wt.-%] | nd | 87.73 |
| bis-(N,N-2-dimethylamino-ethoxyethyl)methylamine | [wt.-%] | nd | 8.81 |
| [2-(2-Amino-ethoxy)-ethyl]-[2-(2-dimethylamino-ethoxy)-ethyl]-methyl-amine | [wt.-%] | nd | 3.46 |

*) = based on water free material
nd = not determined

The structure of bis-(N,N-2-dimethyl-aminoethoxyethyl) amine was verified by GC/MS spectroscopy. The other components were identified as different methylated derivatives of N,N-bis(2-aminoethoxyethyl-)amine, being compounds structurally similar to bis-(N,N-2-dimethylamino-ethoxy-ethyl)-amine.

Bis-(N,N-2-dimethyl-aminoethoxyethyl)amine (optionally after refinement) may further be alkylated, preferably methylated by reacting bis-(N,N-2-dimethyl-aminoethoxyethyl)amine with formaldehyde and hydrogen in presence of a catalyst. As such bis-(N,N-2-dimethyl-aminoethoxyethyl) methylamine (hereafter TM22) is obtained. Purity of above 99% wt of such bis-(N,N-2-dimethyl-aminoethoxyethyl)methylamine may be obtained.

Both T22 and TM22 are assumed to have a boiling point of above 300° C. Boiling points at 7 mbar vacuum of 150 to 152° C. are measured.

In FIG. 1, a reaction scheme is shown for producing, in general, N,N-2-dialkylbisaminoalkylethers from a mixture further comprising at least one of a secondary amine or a tertiary amine, such as at least one of N,N,N'-trialkylbisaminoalkylether and N,N,N',N'-tetraalkylbisaminoalkylether or a mixture of one or more such N,N,N'-trialkylbisaminoalkylethers and N,N,N',N'-tetraalkylbisaminoalkylethers.

An example of such process is the provision of a primary amine with formula $R^{11}R^{12}NR^{13}NH_2$, starting from a mixture comprising primary amines with formula $R^{11}R^{12}NR^{13}NH_2$, secondary amines with formula $R^{21}R^{22}NR^{23}NHR^{24}$ and tertiary amines with formula $R^{31}R^{32}NR^{33}NR^{34}R^{35}$, for which each of $R^{11}$, $R^{21}$ and/or $R^{31}$, $R^{12}$, $R^{22}$ and/or $R^{32}$ being alkyl groups chosen from the group consisting of a methyl group, an ethyl group, an iso-propyl group or an n-propyl group;

each of $R^{24}$ and/or $R^{34}$ and $R^{35}$ being alkyl groups chosen from the group consisting of a methyl group, an ethyl group, an iso-propyl group and an n-propyl group;

each of $R^{13}$, $R^{23}$ and/or $R^{33}$ being an alkoxyalkyl group chosen from the group consisting of ethoxyethyl, ethoxy-n-propyl and n-propoxy-n-propyl.

In a first reaction step, schematically shown as reactor 100, a mixture P3 comprising primary, secondary and/or tertiary amine is provided from the starting materials P1 and P2. This reaction may be catalyzed using a suitable catalyst. As an example N,N-dimethylaminoethoxyethanol (P1) and ammonia (P2) may be reacted in a reactor 100 over a copper-chromite catalyst, e.g. $Cu_2Cr_2O_5$ catalyst being barium promoted. An alternative catalyst may be $2CuO.Cr_2O_3$.

So-called copper-chromite catalysts are examples of typical oxidic catalysts of Group I B/VI B of Periodic Table of elements, which are suitable for the first reaction step. Numerous promoters may be used, mainly comprising elements of the Groups I A and II A, IV B, IV A, VIII B. Other suitable catalysts for alcohol amination reaction are supported or non-supported catalysts of the Group of VIII B. Carriers for group VIII B metals are $Al_2O_3$, $SiO_2$, $TiO_2$, activated carbon, etc. Also, it is popular to add different promoters to such catalyst, mainly of the Groups I A and II A, IV B, IV A.

Carriers like $Al_2O_3$, $SiO_2$, $TiO_2$ may show appreciable activity for alcohol amination reactions. Promoters can be added, which are covering a wide range of components.

The partial pressures of N,N-dimethylaminoethoxyethanol (P1), ammonia (P2) and other gasses, such as service gasses to maintain the reactor pressure, e.g. hydrogen and others gasses, may range from 1 to 150 bar, preferably 5 to 15 bar. Reaction temperature may range from 150° C. to 350° C., preferably in the range from 170° C. to 250° C., e.g. 170° C. to 210° C.

The molar ratio ammonia/N,N-dimethylaminoethoxyethanol may range from 0.5 to 20, preferably ranging from 1 to 6. A catalyst load, expressed as LHSV (=liter/liter*h$^{-1}$) based upon the N,N-dimethylaminoethoxyethanol feed, of 0.01 to 2.0, preferably 0.1 to 1 is used. The mixture P3 comprises primary amine T2MBAEE, secondary amine T3MBAEE and tertiary amine T4MBAEE, as well as ammonia, N,N-dimethylaminoethoxyethanol and water.

The mixture P3 is then separated into various fractions P4, P5 and P6, in separation tool 110. This separation tool may be a batch or continuous distillation unit.

As an example, the mixture P3 comprising primary amine T2MBAEE, secondary amine T3MBAEE and tertiary amine T4MBAEE, as well as ammonia, N,N-dimethylaminoethoxyethanol and water, is separated into a light fraction P4, a middle fraction P5 and a heavy fraction P6. A batch type distillation column may be used.

Preferably, to remove the light fraction P4, the temperature of the mixture in the pot may be chosen in the range of 92° C. to 143° C., the temperature of the head of the column may be chosen in the range of 48-98° C. The pressure may be 100 mbar. The column may comprise 15 to 30 trays of structured packing.

Preferably, to remove the middle fraction P5, the temperature of the mixture in the pot may be chosen in the range of 143° C. to 145° C., the temperature of the head of the column may be chosen in the range of 98° C. to 133° C. The pressure may be 100 mbar. The column may comprise 15 to 30 trays of structured packing.

P4 comprises all reaction water and light boiling components, such as morpholine, N-methylmorpholine and others. The middle fraction P5 comprises primary amine T2MBAEE, secondary amine T3MBAEE and tertiary amine T4MBAEE, and N,N-dimethylaminoethoxyethanol. The heavy fraction P6 comprises bis-(N,N-2-dimethyl-aminoethoxyethyl)amine. Bis-(N,N-2-dimethyl-aminoethoxyethyl) amine at a purity of more than 80% w may be obtained. Next to bis-(N,N-2-dimethyl-aminoethoxyethyl)amine, the heavy fraction further comprises JEFFCAT ZR 70 (at an amount less than 0.2 w %), bis-(N,N-2-dimethylaminoethoxyethyl-1)methylamine (also referred to as "TM22" or by UPAC nomenclature: 2,8,14-triaza-5,11-dioxa-2,8,14-trimethylpentadecane, MW 261) in an amount of 0.1 to 18 w %, [2-(2-Dimethylamino-ethoxy)-ethyl]-[2-(2-methylamino-ethoxy)-ethyl]-amine (or by UPAC nomenclature: 2,8,14-triaza-5,11-dioxa-2-methyl-pentadecane) in an amount of 0.1 to 18 w % and [2-(2-Amino-ethoxy)-ethyl]-[2-(2-dimethylamino-ethoxy)-ethyl]-methyl-amine (or by UPAC nomenclature: 2,8,14-triaza-5,11-dioxa-2,8-dimethyl-tetradecane; MW 233) in an amount of 0.1 to 18 w %.

The heavy fraction further may comprise other unknown high boiling components.

The heavy fraction P6 may be worked up in a cleaning tool 180. This cleaning tool may e.g. be a batch or continuous distillation unit.

The cleaning may result in two product streams, i.e. the cleaned product P24, essentially being Bis-(N,N-2-dimethyl-aminoethoxyethyl)amine, and the residue, waste stream P25.

As an example, the heavy fraction P6, comprising bis-(N, N-2-dimethyl-aminoethoxyethyl)amine, was purified by means of distillation in a batch distillation unit comprising structured packing. Next to bis-(N,N-2-dimethyl-aminoethoxyethyl)amine, the product stream P24 further comprises bis-(N,N-2-dimethylaminoethoxyethyl-1)methylamine, [2-(2-Dimethylamino-ethoxy)-ethyl]-[2-(2-methylamino-ethoxy)-ethyl]-amine and [2-(2-Amino-ethoxy)-ethyl]-[2-(2-dimethylamino-ethoxy)-ethyl]-methyl-amine. Amounts of less than 15 w %, typically ion the range of 0.01 w % to 15 w % may be obtained for each of these additional compounds. Also other unknown high boiling components may be obtained.

In the cleaned product stream, bis-(N,N-2-dimethyl-aminoethoxyethyl)amine at a purity of more than 85% w may be obtained.

A batch type distillation column may be used.

Preferably, to purify heavy fraction P6, the temperature of the mixture may be chosen between 170° C. to 175° C., the head temperature may be chosen 151° C. to 152° C. The pressure is 7 mbar. The column may comprise 15 to 30 trays of structured packing.

The fraction of separation tool 110 comprising the primary amine, secondary amine and tertiary amine, such as in the example the middle fraction P5 comprising primary amine T2MBAEE, secondary amine T3MBAEE and tertiary amine T4MBAEE, and N,N-dimethylaminoethoxyethanol, may optionally be further separated, by means of separation unit 120, for separating a mixture P8 of primarily primary amine, secondary amine and tertiary amine, from the other components in the fraction P5 of separation tool 110.

As is shown in the example in FIG. 1, optionally the middle fraction P5 of separating unit 110, comprising primary amine T2MBAEE, secondary amine T3MBAEE, tertiary amine T4MBAEE, and N,N-dimethylaminoethoxyethanol, is further separated, by means of separation unit 120, into the mixture P8 and a heavy fraction P7.

The heavy fraction P7, in case a separation unit 120 is used, comprises N,N-dimethylaminoethoxyethanol. This product stream P7 might be recycled to the input of reactor 100. The fraction P8 comprises substantially all primary amine T2MBAEE, secondary amine T3MBAEE, tertiary amine T4MBAEE provided by the reaction in reactor 100.

In case no separation unit 120 is used P8 is the product stream P5, comprising all primary amine T2MBAEE, secondary amine T3MBAEE, tertiary amine T4MBAEE provided by the reaction in reactor 100, as well as the N,N-dimethylaminoethoxyethanol.

In a next step, the mixture (P8) of primary amine, secondary amine and/or tertiary amine, and optionally the corresponding alkanol, is reacted with an aldehyde or ketone (P9) in reactor 130, for providing a primary amine-based imine, by the Schiff base reaction of the primary amine and the aldehyde or ketone, being part of the reaction product P10. For completion of the reaction, the effluent P10 of the reactor 130 may be processed in a distillation column 140, wherein the vapour stream P11 of the column head is connected to a Dean-Starck trap 141. The Dean-Starck trap condensate is split into water (P13) which is removed from the trap 141, and the ketone or aldehyde (P12), which flows back to column 140. The effluent of column 140 comprises the primary amine-based imine, secondary amine and/or tertiary amine, and the aldehyde or ketone.

In the example shown in FIG. 1, the mixture P8, comprising primary amine T2MBAEE, secondary amine T3MBAEE and tertiary amine T4MBAEE, is reacted with methylisobutylketone MIBK (P9) in reactor 130.

For completion of the reaction, the effluent P10 of the reactor 130 may be processed in a distillation column 140, wherein the vapour stream P11 of the column head is connected to a Dean-Starck trap 141. The Dean-Starck trap condensate is split into water (P13) which is removed from the trap 141, and MIBK (P12), which flows back to column 140.

A batch type distillation column may be used.

Preferably, to complete the formation of the imine, the temperature of the reaction mixture may be chosen between 70° C. and 180° C., preferably ranging from 90° C. to 140° C. The pressure is between 250 mbar and atmospheric. The column may comprise 15 to 30 trays of structured packing.

The head temperature may range from 50° C. to 120° C. at pressure between 250 mbar to atmospheric pressure.

The effluent P14 of the column 140 comprises T2MBAEE-based imine, being {2-[2-(1,3-dimethyl-butylideneamino)-ethoxy]-ethyl}dimethylamine, T3MBAEE, T4MBAEE, and MIBK. In case no separation unit 120 was used, the effluent P14 further comprises N,N-dimethylaminoethoxyethanol.

The effluent P14 is then separated into various fractions P15, P16 and P17, in separation tool 150. This separation tool may be a batch or continuous distillation unit.

As an example, the effluent P14, comprising T2MBAEE-based imine, T3MBAEE, T4MBAEE, and MIBK, is separated into a light fraction P15, a middle fraction P16 and a heavy fraction P17. A batch type distillation column may be used.

Preferably, to remove the light fraction P15, the temperature of the mixture may be chosen in the range of 70° C. to 180° C., more preferred is between 90° C. and 140° C. The pressure is between 250 mbar and atmospheric. The temperature at the head of the column may range from 50° C. to 120° C. at pressures between 250 mbar-atmospheric. The column may comprise 15 to 30 trays of structured packing.

Preferably, to remove the middle fraction P16, the temperature of the mixture may be chosen between 50° C. and 170° C., the temperature of the head of the column may be chosen in the range of 30° C. to 150° C. The pressure at the head of the column may be chosen in a range of 1 mbar to 250 mbar.

P15 comprises the MIBK, which may be returned to the reactor 130 as part of the product stream P9. The middle fraction P16 comprises T3MBAEE and tertiary amine T4MBAEE. The heavy fraction P17 comprises the T2MBAEE-based imine.

The fraction P16 may further be separated into T3MBAEE and T4MBAEE by amidation and transamidation as set out above, in a suitable process train (not shown).

The fraction comprising the primary amine-based imine (in the example P17) is provided to a hydrolisation tool 160 for splitting the imine back into the aldehyde or ketone and the primary amine. This may be done by providing an excess of water (P18) which may partially be the water (P13) which was removed from the Dean-Starck trap 141.

The vapour stream P19 of the hydrolysation tool 160 is connected to a Dean-Starck trap 161. The Dean-Starck trap condensate is split into water (P21) which is returned to the hydrolysation tool 160, and the ketone or aldehyde (P20), which is removed from the trap 161, and which may be reused as part of the aldehyde or ketone provided to the reactor 130 by means of product stream P9. The effluent P22 of the hydrolysation tool 160 comprises the primary amine. A batch type distillation column may be used.

Preferably, to hydrolyse the imine of P17, the temperature of the reaction mixture may be chosen between 50° C. and 170° C. The head temperature may be chosen in the range 50° C. to 102° C. The pressure may be chosen between 250 mbar to atmospheric pressure. The column may comprise 15 to 30 trays of structured packing.

In the example, the fraction comprising the T2MBAEE-based imine P17 is provided to a hydrolisation tool 160 for splitting the imine back into the MIBK and the T2MBAEE. This is done by providing an excess of water P18 which may partially be the water which was removed from the Dean-Starck trap 141.

The vapour stream P19, comprising water and MIBK, of the hydrolysation tool 160 is connected to a Dean-Starck trap 161. The Dean-Starck trap condensate is split into water (P21) which is returned to the hydrolysation tool 160, and MIBK (P20), which is removed from the trap 161, and which is reused as part of the MIBK provided to the reactor 130. In case a separation tool 120 was used, the effluent P22 of the hydrolysation tool 160 comprises T2MBAEE already relatively pure, e.g. more than 99% w purity, e.g. 99.6% w. In case no separation unit 120 was used, the effluent P22 further comprises N,N-dimethylaminoethoxyethanol.

Optimally, the effluent P22 may further be provided to a purifying tool 170, e.g. a batch or continuous distillation unit.

The cleaning may result in two product streams, i.e. the cleaned product P24 and the secondary product stream P23. A batch type distillation column may be used to clean product P24. Preferably, the temperature of inflowing mixture (P22) is 50° C. to 220° C., the temperature in the head of the column may be chosen in the range of 50° C. to 190° C., preferably in the range of 75° C. to 125° C. The pressure at the head of the column may be chosen in a range of 1 mbar to atmospheric, more preferably in the range of 10 mbar to 100 mbar. The column may comprise 15 to 30 trays of structured packing.

It is understood that the above-mentioned scheme as shown in FIG. 1 and as explained by means of the example of production of T2MBAEE, may be adapted or modified by the skilled person to accommodate the needs when other primary amines are produces or are to be separated from its accompanying secondary and/or tertiary amines.

It is to be understood that although preferred embodiments and/or materials have been discussed for providing embodiments according to the present invention, various modifications or changes may be made without departing from the scope and spirit of this invention.

The invention claimed is:

1. A method for separating a primary amine being an N,N-dialkylbisaminoalkylether, from mixtures comprising said primary amine and at least one of a secondary amine being an N,N,N'-trialkylbisaminoalkylether and a tertiary amine being an N,N,N',N'-tetraalkylbisaminoalkylether, the method comprising the steps:

(α) joining said mixture and at least one of a ketone and an aldehyde, wherein said at least one of a ketone and an aldehyde forms an azeotrope with water, for reacting said primary amine with said at least one of a ketone and an aldehyde, thereby providing a primary amine based imine by a Schiff base reaction;

(β) separating the primary amine based imine from said at least one of the secondary or tertiary amine by distillation;

(γ) recovering the primary amine from its primary amine based imine by hydrolysis of the primary amine based imine; and (δ) after recovering the primary amine from its primary amine based imine, removing the at least one ketone or aldehyde from the primary amine and water by azeotrope distillation.

2. A method according to claim 1, wherein said at least one of a ketone and an aldehyde is an aliphatic ketone or an aliphatic aldehyde.

3. A method according to claim 1, wherein said at least one of a ketone and an aldehyde is chosen from the group consisting of cyclohexanone, valeraldehyde, 2-methylcyclopentanone, cyclopentanone, 3-methyl-2-butanone, 2-methylcyclohexanone, 4-methylcyclohexanone, isovaleraldehyde, 3-methylcyclohexanone, trimethylacetaldehyde, 3,3 dimethylbutan-2one, isobutyraldehyde, 2-butanone, 2-methylbutyraldehyde, 4-methyl-2-pentanone, diethylketone, methylbutylketone and methylisopropylketone.

4. A method according to claim 1, wherein the Schiff base reaction step (α) is carried out with a ketone.

5. A method according to claim 4, wherein the ketone is 4-methyl-2-pentanone.

6. A method according to claim 1, wherein the largest difference between the boiling points of the primary amine and the at least one of a secondary amine and a tertiary amine is less than 10° C.

7. A method according to claim 1, wherein the smallest difference between the boiling point of the primary amine based imine and the boiling points of the primary amine, the at least one of a secondary amine and a tertiary amine is more than 10° C.

8. A method according to claim 1, wherein said primary amine has formula $R^{11}R^{12}NR^{13}NH_2$, said secondary amine having formula $R^{21}R^{22}NR^{23}NHR^{24}$ and/or said tertiary amine having formula $R^{31}R^{32}NR^{33}NR^{34}R^{35}$, for which
- each of $R^{11}$, $R^{21}$ and/or $R^{31}$, $R^{12}$, $R^{22}$ and/or $R^{32}$ being alkyl groups chosen from the group consisting of a methyl group, an ethyl group, an iso-propyl group or an n-propyl group;
- each of $R^{24}$ and/or $R^{34}$ and $R^{35}$ being alkyl groups chosen from the group consisting of a methyl group, an ethyl group, an iso-propyl group and an n-propyl group;
- each of $R^{13}$, $R^{23}$ and/or $R^{33}$ a group chosen from the group consisting of —$CH_2CH_2OCH_2CH_2$—, —$CH_2CH_2OCH_2CH_2CH_2$— and —$CH_2CH_2CH_2OCH_2CH_2CH_2$—.

9. A method according to claim 8, wherein each of $R^{11}$ is identical to $R^{21}$ and/or $R^{31}$, $R^{12}$ is identical to $R^{22}$ and/or $R^{32}$ and $R^{13}$ is identical to $R^{23}$ and/or $R^{33}$.

10. A method according to claim 8, wherein said mixture comprises said primary amine, a secondary amine with formula $R^{21}R^{22}NR^{23}NHR^{24}$ and a tertiary amine with formula $R^{31}R^{32}NR^{33}NR^{34}R^{35}$, $R^{24}$ being identical to $R^{34}$.

11. A method according to claim 1, wherein said mixture comprises a secondary amine and a tertiary amine.

12. A method according to claim 11, wherein the method further comprises separating said N,N,N'-trialkylbisaminoalkylether from said N,N,N',N'-tetraalkylbisaminoalkylether by
 a) amidation of N,N,N'-trialkylbisaminoalkylether to obtain an N,N,N'-trialkylbisaminoalkylether-based amide;
 b) separating N,N,N',N'-tetraalkylbisaminoalkylether from the N,N,N'-trialkylbisaminoalkylether-based amide by distillation;
 c) transamidation of the N,N,N'-trialkylbisaminoalkylether-based amide with a transamidation agent selected form the group consisting of ammonia, primary and/or secondary amines with the proviso that the transamidation agent is not N,N,N'-trialkylbisaminoalkylether;
 d) separation of N,N,N'-trialkylbisaminoalkylether from the reaction mixture obtained by said transamidation by distillation.

13. A method according to claim 1, wherein said N,N-dialkylbisaminoalkylether is N,N-dimethylbisaminoethylether.

14. A method according to claim 13, wherein said mixture comprises at least one of N,N,N'-trimethylbisaminoethylether and N,N,N',N'-tetramethylbisaminoethylether.

15. A method according to claim 13, wherein said mixture comprises N,N,N'-trimethylbisaminoethylether and N,N,N',N'-tetramethylbisaminoethylether.

* * * * *